United States Patent [19]

Liprie

[11] Patent Number: 5,800,333
[45] Date of Patent: Sep. 1, 1998

[54] AFTERLOADER PROVIDED WITH REMOTE CONTROL UNIT

[75] Inventor: Samuel F. Liprie, Lake Charles, La.

[73] Assignee: United States Surgical Corporation, Norwalk, Conn.

[21] Appl. No.: 603,272

[22] Filed: Feb. 20, 1996

[51] Int. Cl.$^6$ .................................................. A61N 5/00
[52] U.S. Cl. ..................................................... 600/3
[58] Field of Search ...................................... 600/1–8

[56] References Cited

U.S. PATENT DOCUMENTS

| | | |
|---|---|---|
| 1,753,287 | 4/1930 | Failla . |
| 1,953,915 | 4/1934 | Burgett et al. . |
| 1,954,868 | 4/1934 | Failla et al. . |
| 2,546,761 | 3/1951 | Loftus . |
| 2,904,272 | 9/1959 | Barrett . |
| 3,669,093 | 6/1972 | Sauerwein et al. . |
| 3,848,137 | 11/1974 | Ellis . |
| 3,861,380 | 1/1975 | Chassagne et al. . |
| 3,866,050 | 2/1975 | Whitfield . |
| 4,096,862 | 6/1978 | DeLuca . |
| 4,150,298 | 4/1979 | Brault et al. . |
| 4,220,864 | 9/1980 | Sauerwein et al. . |
| 4,574,196 | 3/1986 | Kampf . |
| 4,584,991 | 4/1986 | Tokita et al. . |
| 4,631,415 | 12/1986 | Sauerwein et al. . |
| 4,692,628 | 9/1987 | Sauerwein et al. . |
| 4,733,653 | 3/1988 | Leung et al. . |
| 4,851,694 | 7/1989 | Rague et al. . |
| 4,881,937 | 11/1989 | van't Hooft et al. . |
| 4,881,938 | 11/1989 | van't Hooft et al. . |
| 4,897,076 | 1/1990 | Puthawala et al. . |
| 4,969,863 | 11/1990 | van't Hooft et al. . |
| 5,030,194 | 7/1991 | Van't Hooft . |
| 5,084,001 | 1/1992 | Van't Hooft et al. . |
| 5,092,834 | 3/1992 | Bradshaw et al. . |
| 5,103,395 | 4/1992 | Spako et al. . |
| 5,120,973 | 6/1992 | Rohe et al. . |
| 5,139,473 | 8/1992 | Bradshaw et al. . |
| 5,147,282 | 9/1992 | Kan . |
| 5,199,939 | 4/1993 | Dake et al. . |
| 5,213,561 | 5/1993 | Weinstein et al. . |
| 5,295,959 | 3/1994 | Gurbel et al. . |
| 5,344,383 | 9/1994 | Liping . |
| 5,503,041 | 4/1996 | van't Hooft . |
| 5,503,614 | 4/1996 | Liprie . |
| 5,556,389 | 9/1996 | Liprie . |

FOREIGN PATENT DOCUMENTS

| | | |
|---|---|---|
| 0012004 | 6/1980 | European Pat. Off. . |
| 0152124 | 8/1985 | European Pat. Off. . |
| 0158630 | 10/1985 | European Pat. Off. . |
| 0254351 | 1/1988 | European Pat. Off. . |
| 0366214 | 5/1990 | European Pat. Off. . |
| 3442762 | 6/1986 | Germany . |
| 3643902 | 6/1988 | Germany . |
| 0279814 | 7/1975 | U.S.S.R. . |
| 0649412 | 2/1979 | U.S.S.R. . |
| 0857992 | 1/1961 | United Kingdom . |
| 1295559 | 1/1984 | United Kingdom . |
| 0271844 | 9/1989 | United Kingdom . |
| 9200776 | 1/1992 | WIPO . |

OTHER PUBLICATIONS

Nucletron® Brochure; Remote Afterloading System; Feb. 1988.

*Primary Examiner*—John P. Lacyk

[57] ABSTRACT

A remote control device used with an afterloader for advancing and retracting a dummy wire as well as a treatment wire into and out of a patient which is to be treated with a radioactive element or elements. The remote unit is provided with displays for showing the advancement of a treatment or dummy wire as well as indicating a treatment time. A sensor is provided to indicate that a transport tube through which a treatment or dummy wire will be advanced into the patient is properly connected to the afterloader.

54 Claims, 3 Drawing Sheets

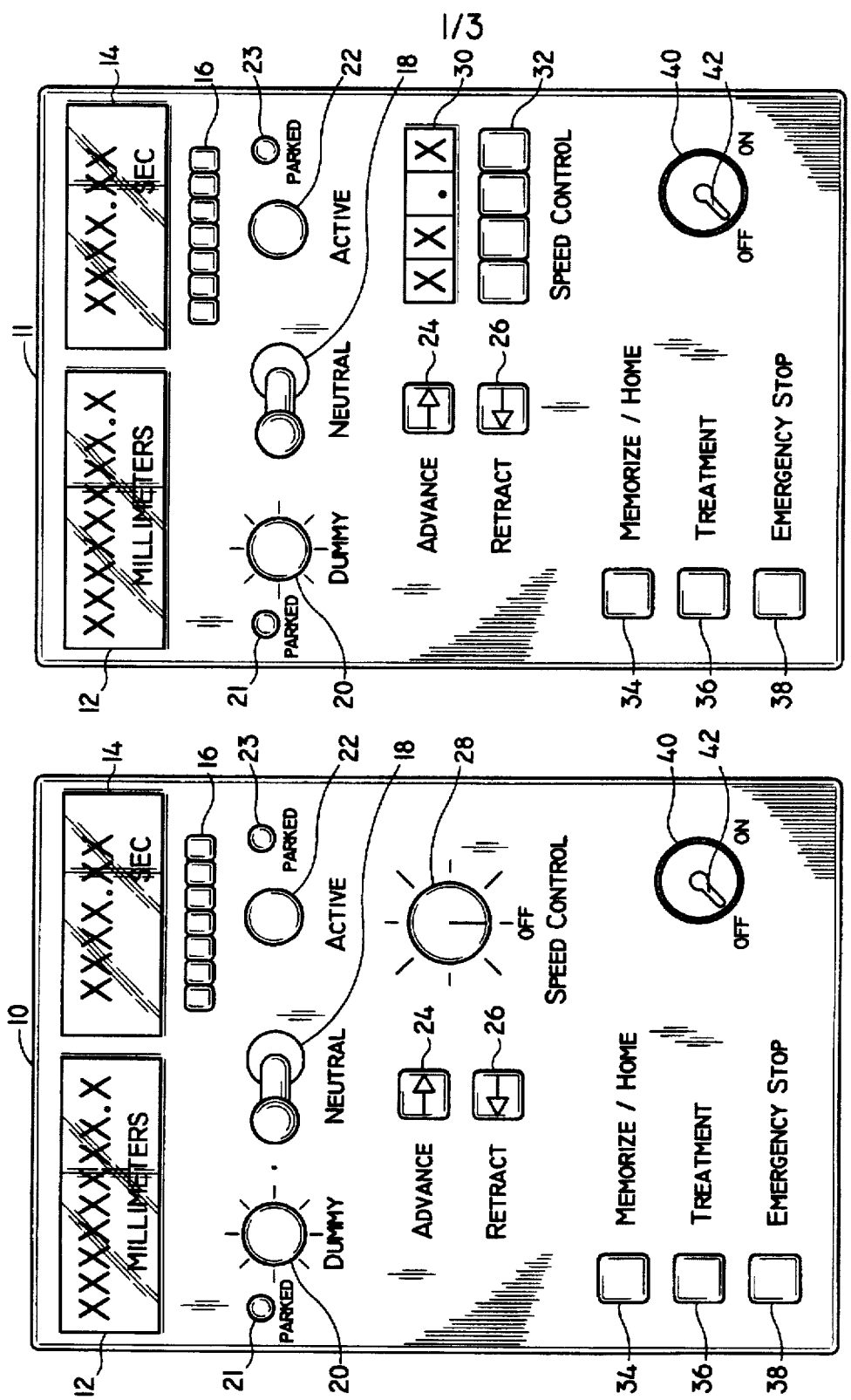

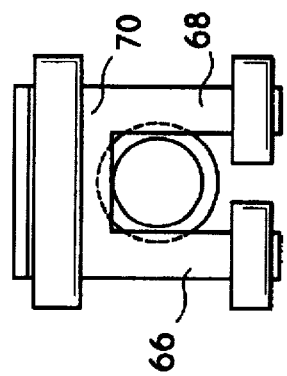
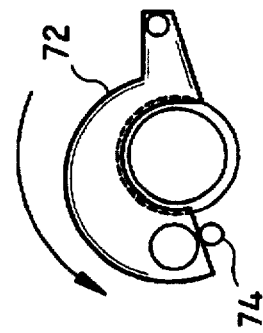
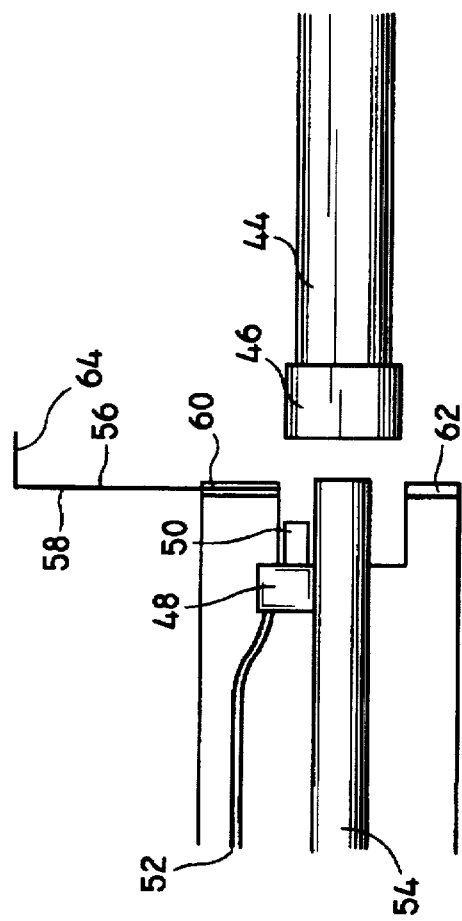
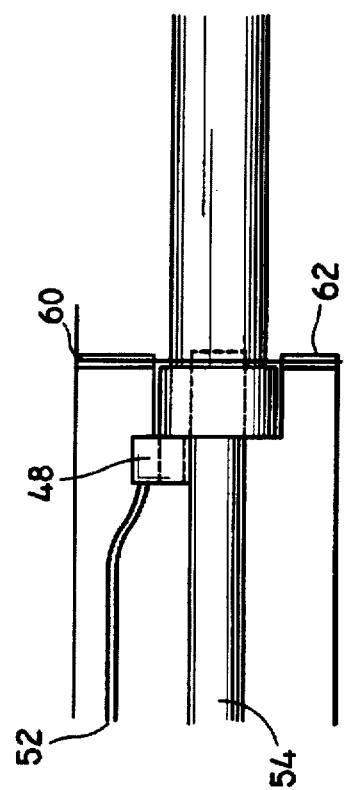

AFTERLOADER PROVIDED WITH REMOTE CONTROL UNIT

FIELD OF THE INVENTION

The present invention relates to remote afterloading devices used to position radioactive treatment source wires inside patients afflicted with cancer or other diseases.

BACKGROUND OF THE INVENTION

Radiation is used to treat cancer and other diseases of the body. Brachytherapy, is a general term for the radiation treatment of cancer at close distances inside the body. During brachytherapy, a radioactive source or sources are positioned in the area needing treatment. Depending on the type of therapy, the radioactive sources are placed permanently inside the body during surgery, or transport tubes (treatment catheters) are placed in the body which are later temporarily loaded with radioactive sources. This temporary afterloading of radioactive material either involves a human handling the radioactive material and receiving radiation exposure, or a machine called a "remote afterloader" that will load and unload the radioactive material into and from the transport tubes. An individual operates the afterloader from a remote location so the individual will not receive any radiation exposure. The focus of this application will be on field of remote afterloaders.

Remote afterloaders are devices generally used in the cancer field to accurately advance and retract a flexible drive member containing a radioactive source over a specified distance for a specified time period. A remote afterloader generally consists of a flexible simulation drive member, a flexible drive member containing a radioactive element, controllers and drive mechanisms to operate both types of flexible members, a shielding safe for the radioactive element, an internal timer, and an exit port attached to a rotating wheel that allows multiple transport tubes (previously placed into the patient) to be hooked up to the device at the same time. The remote afterloader usually sends out the simulation member to check the patency of the transport tube without subjecting the patient to undue radiation exposure, and than sends out the radioactive element. After the treatment is performed in the first transport tube, the afterloader retracts the source into the shielding safe inside the afterloader, a wheel turns and aligns a slot containing the second transport tube to an exit port. The remote afterloader than repeats its function sending and retracting the simulation member and radioactive member through this second tube. The procedure is repeated until the function is carried out through all the specified transport tubes. Since the remote afterloaders use a fixed, short length radioactive source, the afterloaders must multi-step this source many times inside each transport tube to cover the diseased area.

The current remote afterloaders on the market require the following complicated procedures before any treatment can take place:

Initially, by hand, physical measurements must be made of each transport tube after it has been positioned inside the body using a simulation member, fluoroscopy, and a calibrated ruler. These measurements must accurately relate the physical distance the radioactive source needs to travel from the distal end of each tube to the inside of each transport tube to treat the disease inside the body.

Secondly, two 90 degree X-Rays showing all the transport tubes inside the body must be made and digitized into a treatment planning computer. The physical length measurements taken prior to the X-rays, must be matched up with each digitized transport tube in the treatment planning computer and the physical length measurements along with other treatment data must be entered for each transport tube.

The computer than compiles all the data and a treatment plan is formed and stored on a magnetic computer disk.

This computer disk containing the treatment plan is than entered into a treatment computer that programs and operates the remote afterloader. Finally, the treatment takes place.

In most cases, the above setup steps take thirty minutes or more. The use of remote afterloaders were primarily designed for the treatment of cancer but can be used in other treatments of diseases. There are critical factors that will not allow the current remote afterloaders to be used in the treatment of certain types of diseases. The main limiting factor is the long setup time required for treatment. In treatments where time is of the essence, such as restenosis used to treat heart patients, a long setup time could literally mean life or death for the patient. The present invention allows a specially designed remote afterloader to perform its duty in a much less time period, eliminating many of the time consuming steps.

Other limiting factors of prior art treatment afterloaders are the physical size and amount of equipment necessary to operate a remote afterloader. In many treatment facilities, there is not enough room for this amount and size of equipment. Lack of certain safety features, such as an indirect but not a direct transport tube sensing device to ensure that the transport tube is properly connected to the afterloader, human error when measuring and translating treatment distance, no control of the speed in which the drive members move, no means to fine tune the position of the drive members once they reach their target area, along with the lack of other safety features make the current remote afterloaders limited in use and effectiveness.

Thus, there exists a need for a simple, compact, portable, self-contained remote afterloader that can treat a patient with little or no setup time, and contains improved safety features.

It is an object of the present invention to provide a portable, self-contained, remote afterloader that will be easy to maneuver and is compact in size.

It is another object of the present invention to provide handheld controls instead of bulky workstations and computers.

It is another object of the present invention to provide safety features of an improved afterloader that can directly sense proper connection of the transport tube (treatment catheter) to the afterloader.

It is another object of the present invention to provide direct control of the speed in which the drive members move in and out of the afterloader.

It is another object of the present invention to allow for direct measurement and translation of the treatment distance, eliminating chance of human error.

Still another object of the present invention is to allow for fine tune adjustment of the drive member once it has reached its intended target.

SUMMARY OF THE INVENTION

These and other deficiencies of the prior art are addressed by the present invention which is directed to a remote afterloader that is self-contained, compact in size, requires very little setup time and has improved safety features.

The remote afterloader will be a simple one channel device employing a single treatment tube that will be used primarily for treatment of disease at short distances from the radial center of a fixed length source. For example, 99% of the restenosis in heart patients are 1.5 centimeters or less in length. A fixed length, reusable, radioactive source which is three centimeters in length would be able to treat greater than 99% of the vascular disease encountered at the time of the angioplasty. Other afterloading devices micro-step a 0.5 millimeter or less (in length) radioactive source and require two X-Rays showing all the transport tubes positioned in the body, from 90 degree angles, a digitizer to convert the X-Rays which are transmitted to a treatment planning computer and a separate treatment computer to operate the remote afterloader. The remote afterloader according to the present invention will eliminate all of this, since a simple chart (based on the activity and length of the source) would easily display the treatment time required for each radius distance.

Current remote afterloaders require a physical measurement to be made of each transport (or treatment) tube, by taking a simulation wire, and positioning the wire inside the transport tube by use of fluoroscopy, marking the wire where is exits the transport tube, and physically measuring the wire on a calibrated ruler. These measurements must be recorded and matched up precisely with each transport tube in the X-Ray films, and entered into the digitized treatment planning computer prior to a treatment plan being generated.

The remote afterloader, according to the present invention, eliminates all of the above steps. The transport (treatment) tube is connected to the afterloader and by simply using one of the two hand-held remote controls, a dummy (simulation) drive member is advanced into position through a connector port of the afterloader and into the body of the patient by direct verification under fluoroscopy. At this point, a "memorize/home" button is pressed and the afterloader memorizes this position and retracts the simulation member to the "zero" (parked or home) position. The treatment time is set either using the remote control unit or by using an external timer on the afterloader. The operator than stands back a safe distance or behind a shield, activates the "active" mode on the remote control, presses the "treatment" button and the active member including the radioactive source is automatically advanced to the memorized position. At the end of the treatment time, the radioactive source portion of the active member is automatically retracted into the shielding safe inside the afterloader. To ensure that the active member is properly advanced from its "zero" (parked or home) position, the proximal end of both the dummy wire and the active wire should be positioned within the afterloader at an equal distance from the connector port. Furthermore, the length of the dummy wire and the active wire should be equal. Although only one remote control is necessary, it is strictly for a safety backup and for convenience that two remote control units are provided.

Instead of bulky equipment such as the digitizer, planning computer, treatment computer, and printers, all that is necessary to operate the remote afterloader is a simple hand-held remote control. This remote control provides many unique features that are simple to use. One feature is a toggle switch that will allow one to switch from the dummy (simulation) mode to the active (radioactive) mode. An appropriate use for this feature, is after the "memorize" button has been activated and one wants to double check the treatment position. As long as the toggle switch is in the dummy mode, the dummy member will go to the memorized position (the treatment timer will not start in the dummy mode). If everything looks good, the toggle switch is placed in the active mode and the treatment and timer begins once the radioactive member reaches the memorized position.

Another feature of the remote control is a direct input on the speed in which the remote afterloader advances and retracts the drive members. By simply turning a knob or pressing a counter encompassing a speed control for the drive member, the speed of the drive member instantly decreases or increases. This is especially useful if a fine tune position adjustment of a drive member is needed. At any time, the position of the dummy or active member, can be fine tuned if necessary, by simply pressing the advance or retract button on the remote control. This fine tuning feature would allow the drive member to be advanced or retracted only a small distance, such as a fraction of a millimeter. This is accomplished by setting the speed control at a very low speed and quickly pressing the advance button or retract button. As long as the speed control is set at this very low value when either the advance button or the retract button very quickly, the drive member will move only a very small or precise distance. Repeating this fine tuning procedure will place the drive member precisely where indicated.

The remote control also features a direct distance display of the drive member as it is moving, a display of the treatment timer as it is counting down, as well as an emergency retract button. When the emergency retract button is pressed, the timer instantly stops and the active member retracts into the shielded safe. If the afterloader is operating properly, pressing the treatment button again will send the active member to the proper location and the timer will resume from where it left off once the active member reaches its treatment position.

There are several safety features used to assure that both of drive members are parked precisely in position in the afterloader. The remote afterloader contains optical sensors behind the parked (home or zero) position. Prior to each treatment, the drive mechanism "zeros" each drive member by retracting the drive member (dummy or active treatment wires) until the optical sensors do not sense the drive member. At this point, the drive mechanism immediately stops and advances the drive member until it is sensed by the optical sensor, and than advances the drive member a specified distance to the home (zero) position. An encoding system is also connected to each drive member as another backup safety device. During the aforementioned zeroing procedure, if the optical sensors were to fail, the encoding system would not allow the retraction of the drive members past a certain point. For example, the optical sensor associated with the active drive member is located inside the shielding safe, but distal to the radioactive segment of the active drive member. If the optical sensor was to fail, the encoding system would not allow the radioactive segment to be retracted from the distal end of the safe. The encoding system would register an "error and code number" on the distance display window of the remote control, indicating the problem. The radioactive core would still be safely contained inside the shielding safe of the afterloader.

Another safety feature is that, during the retraction of a drive member from a transport tube, the encoding system will temporarily stop the drive member at the same number of counts from where it started and then the zeroing feature will be implemented. For example, if the encoding system counted 5020 counts for a drive member when it was advanced forward, it will count down to exactly 5020 counts on the retraction, stop the movement, and the zeroing function will take over. This is a safeguard from the member being retracted too fast into the afterloader and overriding the zeroing capabilities.

The encoding system also monitors the drive member for slippage and accuracy. The encoding system corrects for both many times a second as the drive member is being advanced and retracted.

Prior art afterloaders use an indirect method to check that a transport tube is properly connected. A separate connector grips a transport tube and then locks it into the afterloader. This connector has a plunger that extends from the connector's distal end when a transport tube is placed into the connector's proximal end. A optical sensor inside the afterloader senses this extended plunger and indicates to the afterloader it is possible to send out the drive member. As the connector becomes weak, or full of debris, the plunger can extend and indicate that a transport tube is in place when in actuality, a transport tube is not even present. There are many times when a transport tube has fallen out of this type of connector due to a weak grip or improper hook-up. If the machine sends out a radioactive member and no transport tube is present a dangerous situation can occur.

To eliminate the problem, the present invention employs a direct sensing mechanism that will indicate that the transport tube is properly connected directly to the afterloader. The hub of the transport tube will slide into the connector port of the afterloader, connect to the drive tube through which the drive member exits, and depress a pressure sensor or mechanical switch. A locking mechanism on the afterloader such as a slotted plate, will lock against the outside of the hub or onto the transport tube to hold the transport tube in place. A gripping apparatus similar to the device that holds a drill bit inside a drill could also be used to lock onto the tubing to lock the transport tube to the afterloader. The pressure sensor or mechanical switch must indicate a certain amount of pressure, or be depressed, or electronics of the afterloader will cause the drive members to be in their zero (parked) positions. Unless the transport tube is properly positioned, the afterloader will not allow the drive members to move from their zero position.

BRIEF DESCRIPTION OF THE DRAWINGS

For a more complete understanding of the present invention, and the advantages thereof, reference is now made to the following descriptions taken in conjunction with the accompanying drawings, in which:

FIG. 1 is a view of the remote control unit of the present invention showing the displays and functions;

FIG. 2 is a similar view of the remote control in FIG. 1, showing a different means to program the speed in which the drive members travel;

FIG. 3 is a partial cross-section of the connector port exiting the end of the remote afterloader, showing a pressure or mechanical switch, a locking mechanism in the open position, and a transport tube ready to be connected to the remote afterloader;

FIG. 4 is a partial cross-section demonstrating the proper connection of the transport tube to the remote afterloader;

FIG. 5 is a frontal view showing a first embodiment of the locking mechanism holding the transport tube in place;

FIG. 6 is a frontal view showing a second embodiment of the locking mechanism holding the transport catheter in place.

DETAILED DESCRIPTION OF THE PREFERRED EMBODIMENTS

Figure 7:
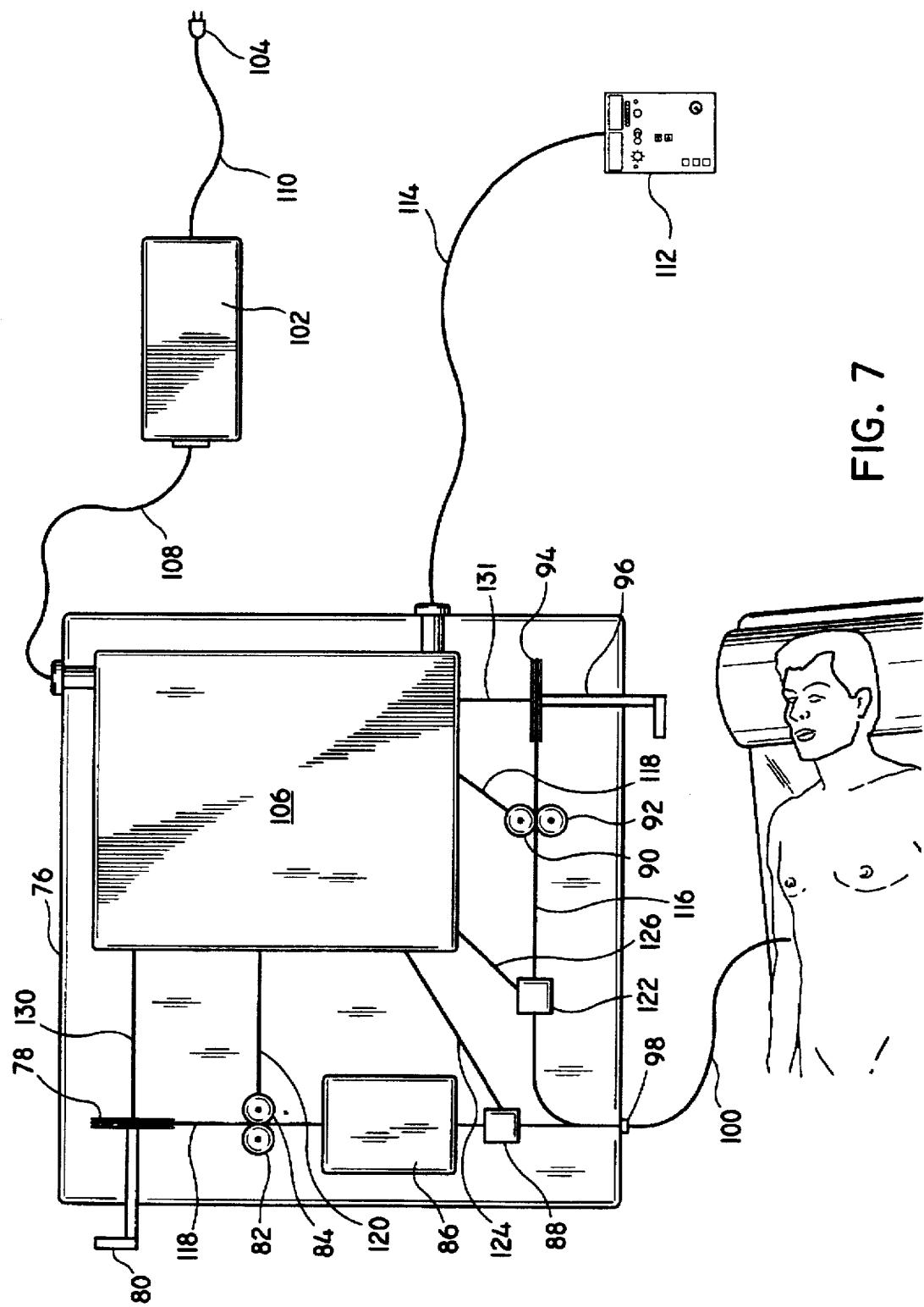
FIG. 7 is a schematic view of the afterloader connected to a patient.

The present invention relates to the improved design and manufacture of remote afterloaders. The invention relates to a novel, compact, lightweight, easily portable, self-contained, afterloading unit that can easily fit into the trunk of a small car and be moved from site to site. Afterloading units on the market today are too bulky or cumbersome to be easily transported. All current afterloading units are very expensive, bulky in size, and require a great amount of extra equipment including computers, a digitizer, and printers. They also require a special hook-up to workstations in order for the afterloader to operate correctly.

The set-up procedure for prior art afterloaders is complicated and time consuming, making them unusable for treating many types of diseases in which time is a critical factor. The present invention is a simpler design with very little set-up time and improved safety features. The present invention is operated either through direct AC power or by an uninterrupted power supply (UPS), in case of a power failure. Although the present invention is designed primarily for the treatment of vascular restenosis, it can be used to treat other diseases of the body, such as cancer.

Referring now to the drawings, and initially to FIG. 1, it is emphasized that the Figures, or drawings, are not intended to be to scale. FIG. 1 illustrates a hand-held remote control unit 10. This is the only equipment needed to operate the remote afterloader. The remote control unit 10 includes several displays and unique features pertaining to the use of remotely controlling the operation of the afterloader. For example, a direct distance readout 12 of a flexible drive member as it travels through the transport tube is provided. The distance readout can be programmed to display counts, centimeters, inches, or fractions thereof. A second display feature 14 provides a direct readout of treatment time. It will count down from the total time in seconds to perform a treatment procedure. The count down timer can be programmed by depressing the corresponding buttons 16 below the display or by an external count down timer on the afterloading unit.

The remote control unit includes a toggle switch 18 or similar device that will enable the operator to control either the dummy (simulation) drive member or the active (radioactive) drive member. A neutral position is also provided that allows the afterloader to be turned on and prevents any communication between the remote control and the afterloader. A green light 20 or other colored or similar display device is illuminated when the toggle switch 18 is in the dummy mode, and a red light 22 or other colored or similar display device is illuminated when the toggle switch 18 is in the active mode. A green light 21 or other colored or similar display device is illuminated when the dummy drive member is in its "parked" (home) position inside the afterloader. A green light 23 or other colored or similar display device is illuminated when the active drive member in its "parked" (home) position inside the afterloader. When the dummy member is moving, the green light 20 will flash. When the active member is moving, the red light 22 will flash. No lights other than the parked lights 21 and 23 (if the drive members are in their parked (home) position) will be illuminated if the toggle switch 18 is in the neutral position. To advance either the dummy or the active member, the toggle switch 18 must be in the correct corresponding mode and an advance button or similar control 24 must be depressed or engaged. To retract either the dummy or the active member, the toggle switch 18 must be in the correct corresponding mode and the retract button 26 or similar device must be depressed or engaged.

The speed in which the drive mechanisms advance and retract the dummy or active member is controlled from a rotatable knob 28 (rheostat) as in FIG. 1, or from a series of programmable push buttons 32 as indicated by the remote unit 11 shown in FIG. 2. This feature is very important for fine tuning the placement of either the dummy or the active member. The actual speed of the drive mechanisms controlled by the speed control 32 is illustrated in display 30.

The next control is a push button 34 labelled "Memorize/Home". This control is used once the exact placement of the dummy member in the simulated treatment position is obtained. Normal use of the controls will be as follows: The distal end of a transport tube will be placed inside the body and the proximal end will be connected to the remote afterloader. The toggle switch 18 will be placed in the dummy position. Depression of the advance button 24 and turning or programming the speed control will drive the dummy member into position within the body of the patient. Fluoroscopy is used to monitor the movement of both of the drive members. As the dummy member approaches the target area in the body, it is advisable to decrease the speed so a precise placement of the dummy member in the treatment area can be obtained. Releasing the advance or retract button 24 or 26 immediately stops the member movement. Once optimal placement is achieved, the memorize/home button 34 is depressed which would immediately memorize the exact position of the dummy member and retracts the dummy member to its zero (parked or home) position. The treatment timer 16 is set for the total treatment time. The position of the dummy member can be checked as many times as needed by pressing a treatment button 36. The count down timer will not start as long as the toggle switch 18 is in the dummy (or neutral) position. The real treatment begins by placing the toggle switch 18 in the active position and pressing the treatment button 36. The afterloader automatically advances the active member to the memorized position. Once the active member is in position, the count down timer starts. When the count down timer reaches zero, as shown in display 14, the afterloader automatically retracts the radioactive segment of the active member into a shielding safe located inside the afterloader.

If an emergency develops, pressing an emergency stop button 38 automatically stops the timer and retracts the active member into the shielding safe inside the remote afterloader. Once the emergency has passed, the positioning can be rechecked by placing the toggle switch in the dummy mode and pressing the treatment button 36. If everything is in order, the treatment can resume where it left off, by placing the toggle switch in the active mode and pressing the treatment button 36. The active member will travel to the memorized position and the treatment timer will resume where it left off.

A final safeguard on the remote control is a key lock 40. A key must be inserted into a slot 42 in the remote control and turned to the "On" position or no communications from the remote control to the afterloader is possible.

FIG. 3 illustrates a sensing device that directly senses the presence of a transport tube (treatment catheter) 44 provided with an enlarged hub 46 at one end. A connector port on the remote afterloader has a place to hook the transport tube 44 from the patient to the remote afterloader. A mechanical switch 48 provided with a pressure sensing device 50 is located inside the connector port of the remote afterloader and is in direct communications with the electronics that are responsible for the movement of the drive members via wires 52. Alternatively, non-hard wired communication can be used. FIG. 3 shows the mechanical switch or pressure sensing device in the open position. In this open position the afterloader will not allow the drive members to move from their zero (home) positions. FIG. 3 also shows a locking mechanism 56 that will hold the transport tube 46 in place. In this figure the locking mechanism in the unlocked position.

FIG. 4 illustrates the correct hook-up between the transport tube 44 and the remote afterloader. The pressure sensing device 50 of the switch 48 is depressed and the transport tube is locked firmly to the afterloader by a slide plate 58 with an opening too small to allow the hub 46 of the transport tube to pull through. Since the pressure sensor is depressed, a signal is sent to the controller electronics to allow movement of one of the drive members through an exit port 54 and then through the transport tube 44. The signals are monitored many times a second by the controller electronics. If for some reason the drive member (dummy or active) was advanced and the transport tube becomes detached from the connector port, the sensor 50 would immediately detect that no transport tube was present and signal the controller to immediately retract the drive member to its zero (home or parked) position. An error message with a code number (indicating the problem area) would show up on the distance or count display 12.

FIG. 5 illustrates the locking device as described in FIG. 4 firmly holding the transport tube in the locked position. The locking device includes the sliding plate 58 that fits into horizonal guiding channels 60, 62 located adjacent to the exit port of the remote afterloader. The sliding plate contains a lip 64 for proper seating in the top horizontal guiding channel 60. The sliding plate can contain an opening large enough to allow the tubing section of the transport tube to pass, but not the hub of the transport tube, or it can bite or grip onto the wall of the tubing section of the transport tube. This opening is created by providing two horizontal portions 66, 68 connected to a vertical portion 70.

FIG. 6 illustrates a locking device similar in function to FIG. 5. Instead of a sliding plate that fits into horizonal channels, a rotating plate 72 will rest on a stopper 74, which lines it up with a threaded hole on the remote afterloader and the end of the rotating plate locks to this threaded hole by means of a threaded screw. This rotating plate, like the locking device in FIG. 5, can contain an opening large enough to allow the tubing section of the transport tube to pass, but not the hub of the transport tube, or it can bite or grip onto the wall of the tubing section of the transport tube.

FIG. 7 illustrates an afterloader 76 which is used in conjunction with the remote controller of the present invention to treat a patient with radioactive material. This afterloader is powered by an uninterruptable power supply (UPS) 102 which is connected to the afterloader 76 by a standard wire or cable 108. The UPS 102 is connected, by a standard wire or cable 110 to a standard plug 104 which would be inserted into an electrical outlet. Both the UPS 102 as well as the remote units 10, 11 (noted by 112 in FIG. 7) are connected to a controller unit 106 via a standard wire or cable 114. The controller 106 is provided within the afterloader unit and would include suitable electronics including a solid state memory unit for controlling the operation of the afterloader. It is noted that the controller 106 could be provided with an internal power supply, such as a series of rechargeable batteries. In this instance, the UPS 102 becomes unnecessary. Furthermore, a wireless communication link can be established between the remote unit 112 and the controller 106, eliminating the need for wire or cable 114. Typically, an infrared or radio frequency signal can be utilized in this mode.

The afterloader 76 includes a dummy wire 116 which would be inserted into a patient to determine the correct treatment position. This wire 116 is provided on a pulley 94. Drive rollers 90, 92 would allow the dummy wire 116 to be advanced through the afterloader, out of a connector 98 shown in FIGS. 3 and 4 and into the patient through treatment tube or catheter 100. One or both of the drive rollers 90, 92 can be provided with an encoder used to display the exact position of the dummy wire 116 within the body of the patient. The encoder would read the moving wire by direct contact or by direct attachment to a moving mechanism that is in direct contact with the moving wire. The encoder is in direct contact with the controller 106 by a wire 118 or other means of conveying information from the encoder to the controller 106. An optical sensor or mechanical switch 122 detects the proximal end of the wire and sends a signal to the controller 106 via a wire 126. The controller 106 uses this information in combination with the signals from the encoder to position the dummy wire in its "zero" or "parked" home position. The distal end of the wire wraps around a pulley 94 which moves in unison with the drive rollers 90, 92. The controller 106 uses signals from the encoder to control the movement of the pulley 94 via a wire 131 so that excess wire can be safely stored in a coiled manner until needed. The pulley system has a forward built-in brake system that will not allow the drive rollers to advance the wire completely from the pulley. The pulley also contains a reverse built-in brake system that will not allow the rollers to retract the wire beyond its home position. This brake system could be a mechanical lock that will only allow a set amount of rotation before a peg or rod would rest against an adjustable (determined by the overall length of the wire) stop and not allow further rotation. When the peg rests against the stop, a signal is sent to the controller to immediately stop rotation of the drive roller. At this point, if necessary, the operator can send a signal from the remote unit 112 to the controller 106 to retract the wire if the forward brake system is engaged, or send the signal to advance the wire if the reverse brake system is engaged.

The afterloader also includes an active treatment wire 118, a pulley 78, drive rollers 82, 84, at least one encoder, and an optical sensor or mechanical switch 88 which would operate in the manner just described with respect to the dummy wire transport system. Information from an encoder provided proximate to the rollers 82, 84 is transmitted through the controller 106 by a wire 120. Additionally, information from the optical sensor 88 is transmitted to the controller 106 via a standard wire 124. The controller 106 uses signals from the encoder to control the movement of the pulley 78 via wire 130 so that excess wire can be safely stored in a coiled manner until needed. A shielded safe 86 is included through which the treatment wire 118 will pass. This treatment wire includes a radioactive element or elements which would be used to treat the patient. When the treatment wire is retracted into the afterloader, the radioactive element or elements would be stored in the safe 86 when the treatment wire is in its home position. It is noted that the optical sensor 88 is located proximal to the shielded safe 86, but could be positioned in the shielded safe.

The aforementioned emergency stop button 38 would operate in conjunction with either an emergency retraction device 80 for retracting the radioactive treatment wire 118 into the safe 80, or with retraction device 96 for retracting the inactive dummy wire 116 to its home position within the afterloader. These retraction devices can also be operated manually.

The present invention has thus been described, but it is desired to be understood that it is not confined to the particular forms or uses as shown and described, the same being merely illustrative, and that the invention may be carried out in other ways without departing from the spirit of the invention. Therefore, the right is broadly claimed to employ all equivalent instrumentalities coming within the scope of the claims. It is also maintained that the particular embodiments herein shown and described are only some of the many that can be employed to obtain the results and objects of the present invention.

What is claimed is:

1. A method for treating a patient with a radioactive source wire stored in an afterloader having a connector port, and an electronic controller provided with a memory, comprising the steps of:

attaching a treatment tube to the connector port of the afterloader;

sensing a positive connection between the treatment tube and the connector port;

advancing an inactive treatment wire stored in the afterloader at a home site, through the connector port and treatment tube and into the body of a patient until a treatment site is reached;

determining the distance said inactive treatment wire has advanced from said home site of said inactive treatment wire to the treatment site;

transmitting said distance to the electronic controller;

storing said distance in the electronic controller;

retracting said inactive treatment wire from the treatment site to said home site of said inactive treatment wire;

advancing the radioactive source wire from a home site of the radioactive source wire through the treatment tube to the treatment site utilizing the distance sensed in said determining step;

maintaining the radioactive source wire at the treatment site for a predetermined period of time; and retracting the radioactive source wire from the treatment site to said home site of the radioactive source wire.

2. The method in accordance with claim 1 further including the steps of:

utilizing a first encoder in direct contact with said inactive treatment wire to positively determine the distance said inactive treatment wire has traveled in said determining step; and utilizing a second encoder in direct contact with the radioactive source wire to advance the radioactive source wire from said home site the radioactive source wire to the treatment site a distance equal to the distance determined during said determining step.

3. The method in accordance with claim 2 further including the steps of:

sensing the exact position of said inactive treatment wire after it has been retracted into the afterloader to ensure that it has been returned to its home site; and sensing the exact position of the radioactive source wire after it has been retracted into the afterloader to ensure that it has been returned to its home site.

4. The method in accordance with claim 1 further including the steps of:

sensing the exact position of said inactive treatment wire after it has been retracted into the afterloader to ensure that it has been returned to its home site; and sensing the exact position of the radioactive source wire after it has been retracted into the afterloader to ensure that it has been returned to its home site.

5. The method in accordance with claim 1 further including the step of locking the treatment tube to the connector port.

11

6. A control unit used to remotely operate an afterloader provided with a radioactive source wire, an inactive treatment wire, a connector port through which the radioactive source wire and the inactive treatment wire travel, as well as an electronic controller provided with a memory, comprising:

a communication device operatively associated with the control unit and configured to transmit data to the electronic controller;

a first control device provided in the control unit configured to activate the electronic controller to cause movement of the inactive treatment wire;

a second control device provided in the control unit for entering the distance travelled of the inactive treatment wire into the electronic controller when the inactive treatment wire is advanced to a treatment site in a patient;

a third control device provided in the control unit configured to activate the electronic controller to advance the radioactive source wire the exact distance entered into the electronic controller enabling the radioactive source wire to be advanced to the treatment site in a patient; and a speed control device for regulating the speed of movement of the radioactive source wire and the inactive treatment wire.

7. The control unit in accordance with claim 6 wherein said speed control device is digital.

8. The control unit in accordance with claim 6 wherein said speed control device is analog.

9. The control unit in accordance with claim 6 further including a fourth control device for immediately retracting the radioactive source wire or the inactive treatment wire to its respective home position within the afterloader.

10. The control unit in accordance with claim 6 including a display device for indicating whether the radioactive source wire or the inactive treatment wire is in movement.

11. The control unit in accordance with claim 6 including a display device for indicating the distance the radioactive source wire or the inactive treatment wire has moved to the treatment site.

12. The control unit in accordance with claim 6 including a display device for indicating a treatment time.

13. The control unit in accordance with claim 6 wherein said communication device is a wire.

14. The control unit in accordance with claim 6 wherein said communication device is a radiofrequency link.

15. The control unit in accordance with claim 6 wherein said communication device is an infrared link.

16. The control unit in accordance with claim 6 further including a fifth control device for setting a treatment time.

17. The control unit in accordance with claim 6 wherein the control unit is hand held in size.

18. A control unit used to remotely operate an afterloader provided with a radioactive source wire, an inactive treatment wire, a connector port through which the radioactive source wire and the inactive treatment wire travel, as well as an electronic controller provided with a memory, comprising:

a communications device operatively associated with the control unit and configured to transmit data to the electronic controller;

a first control device provided in the control unit for activating the electronic controller to cause movement of the inactive treatment wire;

a second control device provided in the control unit for entering the distance travelled of the inactive treatment wire into the electronic controller when the inactive treatment wire is advanced to a treatment site in a patient;

a third control device provided in the control unit for activating the electronic controller to advance the radioactive source wire the exact distance entered into the electronic controller, initiated by said second control device, enabling the radioactive source wire to be advanced to the treatment site in a patient; and means provided in the control unit for fine tuning the position of the radioactive source wire and the inactive treatment wire.

19. A device for treating a patient including:

an afterloader unit provided with a radioactive source wire, an inactive treatment wire, an exit port through which said radioactive source wire and said inactive treatment wire pass, a first encoder for sensing the distance said inactive treatment wire travels, a second encoder for sensing the distance said radioactive source wire travels, and electronic controller provided with a memory connected to said first encoder and said second encoder;

a communication device;

a control unit in communication with said electronic controller through said communication device, said control unit provided at a location remote from said afterloader said control unit further provided with a first control device for activating the movement of said inactive treatment wire, a second control device for entering the distance travelled of said inactive treatment wire into said electronic controller when said inactive treatment wire is advanced to a treatment site in a patient, and a third control device for advancing said radioactive source wire the exact distance entered into said electronic controller initiated by said second control device enabling said radioactive source wire to be advanced to the treatment site in a patient; and a connector configured to attach a treatment tube to said exit port of said afterloader, said connector provided with a mechanical sensor which is directly impinged upon by the treatment tube when the treatment tube is properly inserted into said afterloader through said exit port, said mechanical sensor in communication with said electronic controller.

20. The device in accordance with claim 19 wherein said control unit further includes a speed control device for regulating the speed of movement of said radioactive source wire and said inactive treatment wire.

21. The device in accordance with claim 20 wherein said speed control device is digital.

22. The device in accordance with claim 20 wherein said speed control device is analog.

23. The device in accordance with claim 19 wherein said control unit further includes a means for fine tuning the position of said radioactive source wire and said inactive treatment wire.

24. The device in accordance with claim 19 wherein said control unit further includes a fourth control device for immediately retracting said radioactive source wire or said inactive treatment wire to its respective home position within said afterloader.

25. The device in accordance with claim 19 wherein said control unit includes a display device for indicating whether said radioactive source wire or said inactive treatment wire is in movement.

26. The device in accordance with claim 19 wherein said control unit includes a display device for indicating the distance said radioactive source wire or said inactive treatment wire has moved to the treatment site.

27. The device in accordance with claim 19 wherein said control unit includes a display device for indicating a treatment time.

28. The device in accordance with claim 19 wherein said communication device is a wire.

29. The control unit in accordance with claim 19 wherein said communication device is a radiofrequency link.

30. The control unit in accordance with claim 19 wherein said communication device is an infrared link.

31. The device in accordance with claim 19 wherein said connector is further provided with a locking means for positively attaching the treatment tube to said afterloader.

32. The device in accordance with claim 31 wherein said afterloader includes first and second channels provided above and below said exit port through which said locking means pass.

33. The device in accordance with claim 32 wherein said locking means is a sliding plate.

34. The device in accordance with claim 31 wherein said locking means is a rotating plate.

35. The device in accordance with claim 19 further including a shielded safe in which said radioactive source wire is stored.

36. The device in accordance with claim 35 further including a first optical sensor for determining the position of said radioactive source wire when it is at its home position and a second optical sensor for determining the position of said inactive treatment wire when it is at its home position.

37. The device in accordance with claim 36 wherein said first optical sensor is provided in said shielded safe.

38. The device in accordance with claim 37 wherein said first mechanical switch is provided in said shielded safe.

39. The device in accordance with claim 35 further including a first mechanical switch for determining the position of said radioactive source wire when it is at its home position and a second mechanical switch for determining the position of said inactive treatment wire when it is at its home position.

40. The control unit in accordance with claim 19 further including a fifth control device for setting a treatment time.

41. The control unit in accordance with claim 19 further including a safety device which must be engaged before said inactive treatment wire or the radioactive source will move.

42. The control unit in accordance with claim 41 wherein said safety device includes a key provided in a keyhole.

43. The device in accordance with claim 19, when said control unit is hand held in size.

44. A control unit used to remotely operate an afterloader provided with a radioactive source wire, an inactive treatment wire, a connector port through which the radioactive source wire and the treatment wire travel, as well as an electronic controller provided with a memory, comprising:

a communication device operatively associated with the control unit and configured to transmit data to the electronic controller;

a first control device provided in the control unit for activating the electronic controller to cause movement of the inactive treatment wire;

a second control device provided in the control unit for entering the distance travelled of the inactive treatment wire into the electronic controller when the inactive treatment wire is advanced to a treatment site in a patient;

a third control device provided in the control unit for activating the electronic controller to advance the radioactive source wire the exact distance entered into the electronic controller initiated by said second control device enabling the radioactive source wire to be advanced to the treatment site in a patient; and a safety device which must be engaged before the inactive treatment wire or the radioactive source wire will move.

45. The control unit in accordance with claim 44 wherein said safety device includes a key provided in a keyhole.

46. A device for treatment a patient including:

an afterloader unit provided with a radioactive source wire, an inactive treatment wire, an exit port through which said radioactive source wire and said inactive treatment wire pass, a first encoder for sensing the distance said inactive treatment wire travels, a second encoder for sensing the distance said radioactive source wire travels, an electronic controller provided with a memory connected to said first encoder and said second encoder;

a communication device;

a control unit in communication with said electronic controller through said communication device, said control unit provided at a location remote from said afterloader, said control unit further provided with a first control device for activating the movement of said inactive treatment wire, a second control device for entering the distance travelled of said inactive treatment wire into said electronic controller when said inactive treatment wire is advanced to a treatment site in a patient, and a third control device for advancing said radioactive source wire the exact distance entered into said electronic controller initiated by said second control device enabling said radioactive source wire to be advanced to the treatment site in a patient;

a fourth control device for immediately retracting said radioactive source wire or said inactive treatment wire to respective home positions within said afterloader; and a mechanism for insuring that said radioactive source wire or said inactive treatment wire does not retract beyond its respective home position.

47. The device in accordance with claim 46 wherein said mechanism is a brake unit.

48. A device for treating a patient including:

an afterloader unit provided with a radioactive source wire, an inactive treatment wire, an exit port through which said radioactive source wire and said inactive treatment wire pass, a first encoder for sensing the distance said inactive treatment wire travels, a second encoder for sensing the distance said radioactive source wire travels, an electronic controller provided with a memory connected to said first encoder and said second encoder;

a communication device;

a control unit in communication with said electronic controller through said communication device, said control unit provided at a location remote from said afterloader, said control unit further provided with a first control device for activating the movement of said inactive treatment wire, a second control device for entering the distance travelled of said inactive treatment wire into said electronic controller when said inactive treatment wire is advance to a treatment site in a patient, and a third control device for advancing said radioactive source wire the exact distance entered into said electronic controller initiated by said second control device enabling said radiative source wire to be advanced to the treatment site in a patient, and means for retracting said radioactive source and said inactive treatment wire to their respective home position upon sensing a power failure or a failure of said electronic controller.

49. The device in accordance with claim 48 wherein said means for retracting said radioactive source and said inactive treatment wire is a mechanical crank for rotation only in a retraction direction.

50. In a control unit used to remotely operate an afterloader provided with a radioactive source wire, an inactive treatment wire, and an electronic controller provided with a memory for moving the radioactive source wire and the treatment wire, the control unit having a communication device configured to transmit data to the electronic controller, a first control device configured to activate the electronic controller to cause movement of the inactive treatment wire, and a second control device configured to activate the electronic controller to cause movement of the radioactive source wire, the improvement comprising:

a speed control device for regulating the speed of movement of the radioactive source wire and the inactive treatment wire.

51. In a control unit used to remotely operate an afterloader provided with a radioactive source wire, an inactive treatment wire, and an electronic controller provided with a memory for moving the radioactive source wire and the treatment wire, the control unit having a communication device configured to transmit data to the electronic controller, a first control device configured to activate the electronic controller to cause movement of the inactive treatment wire, and a second control device configured to activate the electronic controller to cause movement of the radioactive source wire, the improvement comprising:

means provided in the control unit for fine tuning the position of the radioactive source wire and the inactive treatment wire.

52. In a control unit used to remotely operate an afterloader provided with a radioactive source wire, an inactive treatment wire, and an electronic controller provided with a memory for moving the radioactive source wire and the treatment wire, the control unit having a communication device configured to transmit data to the electronic controller, a first control device configured to activate the electronic controller to cause movement of the inactive treatment wire, and a second control device configured to activate the electronic controller to cause movement of the radioactive source wire, the improvement comprising:

a safety device provided on the control unit which must be engaged before the inactive treatment wire or the radioactive source wire will move.

53. In a device for treating a patient including an afterloader unit provided with a radioactive source wire, an inactive treatment wire, an exit port through which said radioactive source wire and said inactive treatment wire pass, and an electronic controller for moving the radioactive source wire and the inactive treatment wire, and a control unit provided at a location remote from said afterloader and in communication with the electronic controller through a communication device, the improvement comprising:

a connector configured to attach a treatment tube to the exit port of the afterloader, said connector provided with a mechanical sensor which is directly impinged upon by the treatment tube when the treatment tube is properly inserted into the afterloader through the exit port, said mechanical sensor in communication with the electronic controller.

54. In a device for treating a patient including an afterloader unit provided with a radioactive source wire, an inactive treatment wire, an exit port through which said radioactive source wire and said inactive treatment wire pass, and an electronic controller for moving the radioactive source wire and the inactive treatment wire, and a control unit provided at a location remote from said afterloader and in communication with the electronic controller through a communication device, the improvement comprising:

means for retracting the radioactive source wire or the inactive treatment wire to respective home positions in response to a power failure or a failure of the electronic controller.

* * * * *

UNITED STATES PATENT AND TRADEMARK OFFICE
CERTIFICATE OF CORRECTION

PATENT NO.    : 5,800,333
DATED         : September 1, 1998
INVENTOR(S)   : Liprie It is certified that error appears in the above-identified patent and that said Letters Patent is hereby corrected as shown below:

In the title page, item [73] Assignee: should read – Angiorad, L.L.C., Lake Charles, L a—

Signed and Sealed this

Thirteenth Day of July, 1999

*Attest:*

Q. TODD DICKINSON

*Attesting Officer*        *Acting Commissioner of Patents and Trademarks*